(12) United States Patent
Holt et al.

(10) Patent No.: US 8,443,648 B2
(45) Date of Patent: May 21, 2013

(54) CONTROLLED HUMIDIFICATION CALIBRATION CHECKING OF CONTINUOUS EMISSIONS MONITORING SYSTEM

(75) Inventors: Mark Holt, Emmaus, PA (US); William Eberhardt, Cherry Hill, NJ (US)

(73) Assignee: Babcock & Wilcox Power Generation Group, Inc., Barberton, OH (US)

( * ) Notice: Subject to any disclaimer, the term of this patent is extended or adjusted under 35 U.S.C. 154(b) by 297 days.

(21) Appl. No.: 11/824,089

(22) Filed: Jun. 29, 2007

(65) Prior Publication Data

US 2009/0000349 A1    Jan. 1, 2009

(51) Int. Cl.
*G01N 33/00* (2006.01)
(52) U.S. Cl.
USPC .............................. 73/1.03; 73/1.06; 73/31.05
(58) Field of Classification Search
USPC .............................. 73/1.03, 1.06, 1.07, 31.05
See application file for complete search history.

(56) References Cited

U.S. PATENT DOCUMENTS

| | | | |
|---|---|---|---|
| 3,547,587 A * | 12/1970 | Innes | 436/134 |
| 6,690,462 B2 * | 2/2004 | Seltzer | 356/316 |
| 7,043,958 B2 | 5/2006 | McGee et al. | |
| 7,454,945 B1 * | 11/2008 | Kita et al. | 73/1.03 |
| 2003/0110950 A1 * | 6/2003 | Sjostrom et al. | 96/413 |
| 2004/0103727 A1 * | 6/2004 | Erlach et al. | 73/863.01 |
| 2006/0126056 A1 | 6/2006 | Roberts et al. | |
| 2006/0245973 A1 * | 11/2006 | Kita et al. | 422/68.1 |
| 2006/0246594 A1 | 11/2006 | Appel et al. | |
| 2007/0178015 A1 * | 8/2007 | Schaedlich et al. | 422/100 |

* cited by examiner

*Primary Examiner* — Hezron E Williams
*Assistant Examiner* — Nashmiya Fayyaz
(74) *Attorney, Agent, or Firm* — Eric Marich

(57) ABSTRACT

A continuous emissions monitoring system is in fluid communication with a flue stack conducting exhaust gas from a combustion source. The continuous emissions monitor system comprises an analyzer for measuring concentrations of an analyte present in the exhaust gas. A probe is in fluid communication with the flue stack to acquire a sample of exhaust gas from the flue stack. The probe is also in fluid communication with and located upstream of the analyzer. The probe tends to remove analyte from the sample. A calibration checking system is in fluid communication with the probe. The calibration checking system includes a source that provides a flow of a known concentration of calibration material to be measured by the analyzer. The calibration material is the same as the analyte. A humidifier is associated with the source to provide moisture to a flow of calibration material. The moisture acts to cleanse removed analyte from the probe and thereby enable an accurate measurement of the concentration of the calibration material. A supply system is operatively connected with the humidifier to provide a desired amount of a liquid to the humidifier.

5 Claims, 2 Drawing Sheets

CONTROLLED HUMIDIFICATION CALIBRATION CHECKING OF CONTINUOUS EMISSIONS MONITORING SYSTEM

BACKGROUND OF THE INVENTION

The present invention relates generally to continuous emissions monitoring of exhaust flue gas streams. More specifically, the present invention relates to the humidification of calibration checking in continuous emissions monitoring systems.

The United States Environmental Protection Agency (EPA) identifies sources of mercury (Hg) emissions in the U.S. to be utility boilers, waste incinerators that burn mercury-containing wastes (municipal and medical), coal-fired industrial boilers and cement kilns that burn coal-based fuels. A particularly significant source of mercury emissions is coal-fired power plants.

To quantify the emissions from a particular source, a continuous emissions monitoring system (CEMS) is employed for mercury. There are three forms of mercury in exhaust flue gas stream of a coal-fired power plant that may be monitored by a CEMS. These forms are gaseous elemental mercury, gaseous oxidized mercury and particulate bound mercury that is either elemental or oxidized.

Mercury in the gaseous forms is relatively sticky and has a strong affinity to attach to a wide variety of interior surfaces of CEMS components. Such gaseous mercury is extremely difficult to handle and transport through an extractive gas sampling system to a gas analyzer for measurement. Exhaust flue gases usually contain relatively low concentrations of gaseous mercury that must be detected and the sticky gaseous mercury present readily attaches to surfaces of the components of the CEMS. This renders any measurement made on the sample not truly representative of what is conducted in the exhaust stack.

Particulates and other undesirable material from the stack gas sample might also adhere to surfaces of the CEMS components due to moisture present in exhaust flue gas. This causes the adsorption of elemental mercury onto particles adhered to the wetted surfaces.

The EPA has mandated restrictive controls on mercury emissions. A total mercury measurement is required for regulatory monitoring and the evaluation of mercury control technologies and manufacturing processes requires accurate measurements of gaseous mercury. One example is that the EPA requires a "span gas check" accuracy of plus or minus ten percent (±10%) of a sample range. Accordingly, there exists a need for the development of a reliable and accurate technology capable of verifying the measurement of mercury emitted in an exhaust flue gas stream.

SUMMARY OF THE INVENTION

One aspect of the present invention is directed to a continuous emissions monitoring system that is in fluid communication with a flue stack conducting exhaust gas from a combustion source. The continuous emissions monitoring system comprises an analyzer for measuring concentrations of an analyte present in the exhaust gas. A probe is in fluid communication with the flue stack to acquire a sample of exhaust gas from the flue stack. The probe is also in fluid communication with and located upstream of the analyzer. The probe tends to remove analyte from the sample. A calibration checking system is in fluid communication with the probe. The calibration checking system includes a source that provides a flow of a known concentration of calibration material to be measured by the analyzer. The calibration material is chemically the same as the analyte. A humidifier is associated with the source to provide moisture to the flow of calibration material. The moisture acts to cleanse removed analyte from the probe and thereby enable an accurate measurement of the concentration of the calibration material.

Another aspect of the present invention is directed to an improved continuous emissions monitoring system that is in fluid communication with a flue stack conducting exhaust gas from a combustion source. The continuous emissions monitor system has an analyzer for measuring concentrations of mercury present in the exhaust gas. A probe is in fluid communication with the flue stack to acquire a sample of exhaust gas from the flue stack and in fluid communication with and located upstream of the analyzer. The probe tends to remove mercury from the sample. A calibration checking system is in fluid communication with the probe. The calibration checking system includes a source that provides a flow of a known concentration of a gaseous species of mercury to be measured by the analyzer. A humidifier is operatively connected with the source to provide moisture to gaseous species of mercury flowing through the humidifier. The moisture acts to cleanse removed mercury from the probe and thereby enable accurate measurement of the concentration of the gaseous species of mercury. The improvement comprises a supply system operatively connected with the humidifier to provide a desired amount of a liquid to the humidifier.

Yet another aspect of the present invention is directed to a method of continuous emissions monitoring of a flue stack conducting exhaust gas from a combustion source. The method comprises the steps of acquiring a sample of exhaust gas from the flue stack with a probe. The probe tends to remove mercury from the sample. Concentrations of the mercury are measured with an analyzer located downstream of the probe. The calibration of the analyzer is checked with a flow of a known concentration of calibration material provided by a source. The flow of calibration material is humidified with moisture. The moisture acts to cleanse removed mercury from the probe and thereby enable an accurate measurement of the concentration of the calibration material. A supply system is operatively connected with the humidifier to provide a desired amount of a liquid to the humidifier.

DETAILED DESCRIPTION OF THE INVENTION

A continuous emissions monitoring system (CEMS) for mercury normally consists of a tubular probe assembly located in fluid communication with a flue stack for acquiring a gaseous exhaust sample. The CEMS also includes instrumentation located some distance away from the probe assembly to analyze the acquired sample for the presence of mercury. The relatively small concentration of mercury present in the exhaust gas stream is continuously measured and recorded. Over time, the total amount of mercury emitted is established. Accuracy and precision of the continuous emissions monitoring system are important.

A critical component of the mercury CEMS is the tubular probe assembly located in fluid communication with the stack for taking the sample. The tubular probe assembly can experience multiple problems. Particulate matter is always present in the exhaust stack gas stream and tends to be separated from the exhaust gas and accumulate on surfaces of the tubular probe assembly. Accumulated particulate reduces the accuracy of the mercury measurement. Accumulation of particulates can also result in a reduction of the amount of time the mercury CEMS is accurately measuring emissions in the exhaust gas stream that is mandated by governmental regulation.

The tubular probe assembly is generally U-shaped with an inlet through which gaseous samples are drawn and an outlet through which samples are discharged. An inertial filter may be located near the probe assembly inlet. A venturi eductor is located near the probe assembly outlet and is supplied by a source of clean heated air that exits from the probe assembly outlet into the exhaust stack gas stream. Controlled humidification can be applied to various probe types. It will be appreciated that the probe also can be of a dilution extractive type where the sample is drawn through a filter using a venturi eductor and a critical orifice. Dilution air is introduced at the critical orifice and is used to dilute the extracted sample and mixed with the sample.

This flow of eductor air generates a high velocity (70-100 feet per second) gas flow through the tubular probe assembly, creating a vacuum at the gas inlet. This vacuum at the gas inlet draws the sample stack gas into the tubular probe assembly. Experience has shown that despite the high flow rate, particulate matter does accumulate on surfaces of the probe assembly. This causes inaccuracies of the measurement of mercury concentration in the exhaust gas stream, increasing maintenance and down time when emissions are not being monitored. Since the tubular probe assembly is mounted on the exhaust stack, access to the probe and therefore maintenance of the probe assembly is difficult and time consuming. It is desirable that the probe assembly be as reliable and maintenance-free as possible.

Figure 1:
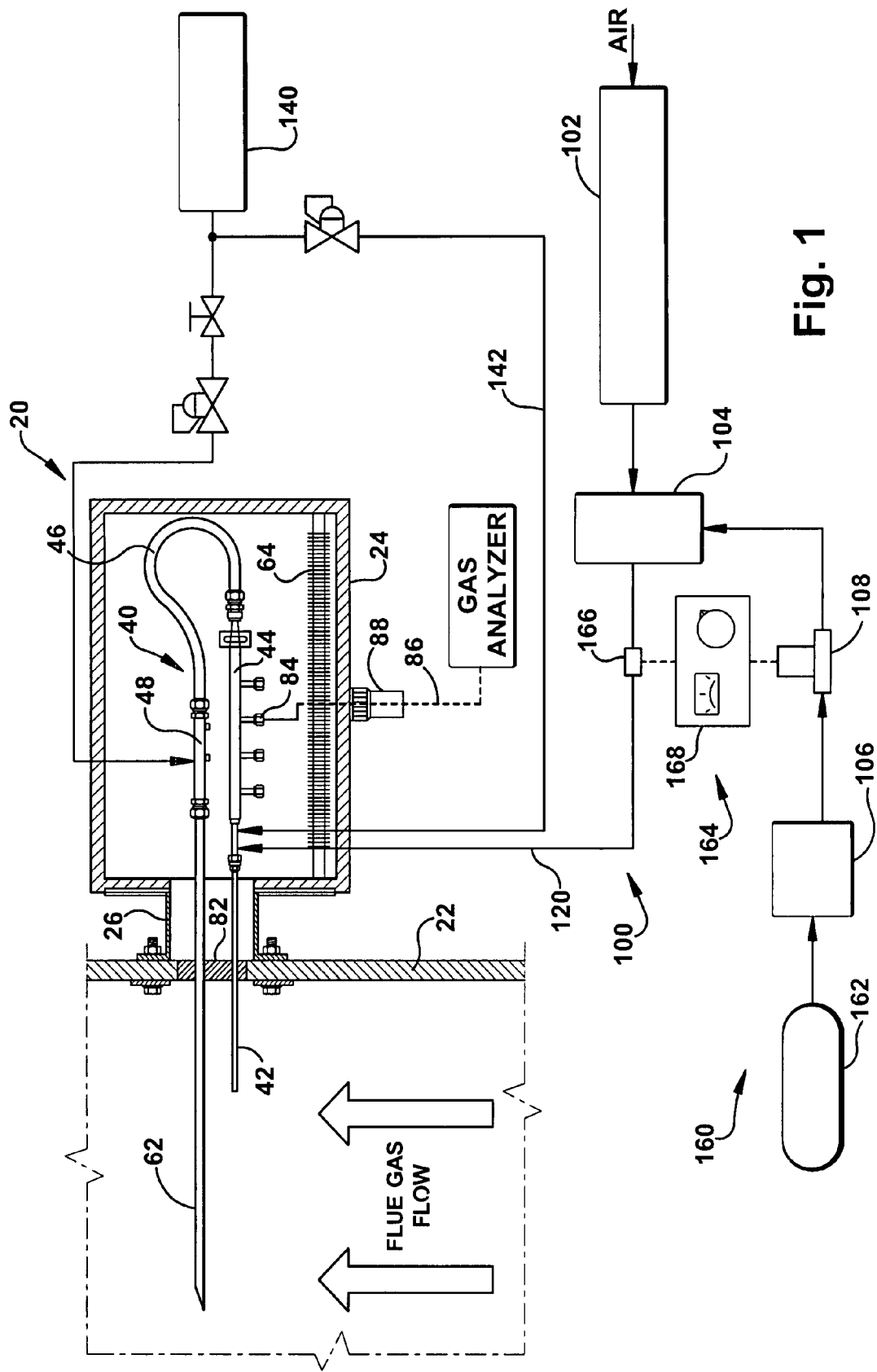
FIG. 1 is a schematic illustration, partly in section, of a system for controlled humidification of calibration checking equipment in a continuous emissions monitoring system according to one aspect of the invention.

A gas sample acquisition apparatus 20 is illustrated in FIG. 1, and includes structure according to one aspect of the invention for checking the calibration of a continuous emissions monitoring system (CEMS) with controlled humidification. The gas sample acquisition apparatus 20 is part of the continuous emissions monitoring system and is operatively connected with a known gas analyzer. Such a gas sample acquisition apparatus 20 and CEMS is suitable for sampling selected pollutants, such as mercury (Hg), that are transported in a flue gas stream flowing in an exhaust stack 22 from a combustion source.

The gas sample acquisition apparatus 20 includes a housing 24 enclosing some components. The housing 24 is made to comply with NEMA standards and is insulated. The housing 24 is attached to the exhaust stack 22 by a tubular connector 26 and may have other attachment structure (not shown).

The gas sample acquisition apparatus 20 also includes a probe assembly 40 mounted in the housing 24. Components of the probe assembly 40 are tubular. The probe assembly 40 includes an inlet or probe tip 42 that is in fluid communication with the flue gas stream in the exhaust stack 22. The probe tip 42 is connected to an inertial filter 44 of the probe assembly 40. The inertial filter 44 is attached to a generally U-shaped stainless steel return pipe 46. The stainless steel return pipe 46 is attached to a venturi flow meter 48. The venturi flow meter 48 is connected to an outlet or probe return 62 that is open to the flue gas flow. The temperature of the gas sample within the components of the probe assembly 40 located in the housing 24 is maintained via a block or jacket heater 64.

The probe tip 42 extends into the exhaust stack 22 through flexible thermal insulation 82. The probe tip 42 draws a sample from the exhaust flue gas flow. The gas sample is transported into the inertial filter 44. The gas sample leaves the inertial filter 44 via the stainless steel return pipe 46. The gas sample then passes through the venturi flow meter 48. Finally, the gas sample leaves the housing 24 by passing through the probe return 62.

During the circulation of the gas sample through the components of the probe assembly 40, a representative sub-sample is drawn from the inertial filter 44 at tap 84. The sub-sample is conducted out of the housing 24 in line 86 extending through port 88 in the housing. The sub-sample is conducted to a gas analyzer for analysis in a known manner. Suitable gas analyzers are well known in the art and include, without limitation, UV atomic absorption and atomic fluorescence detectors.

The inertial filter 44 is typically made from a tubular sintered metal material. The sintered metal of the inertial filter 44 has a relatively large surface area. The surfaces of the inertial filter 44 act to contact particulates in the exhaust gas which tend to then remove mercury from the exhaust gas by adsorption. Particulates and other undesirable material from the stack gas sample might adhere to the wetted surfaces of the probe and cause the adsorption of elemental mercury onto particles adhered to the wetted surfaces. This affects the concentration of mercury, or analyte, that the gas analyzer is exposed to and is, therefore, not a true measure of the concentration of mercury in the exhaust gas.

To minimize particulate matter from accumulating on surfaces of the components of the probe assembly 40 of the gas sample acquisition apparatus 20 a calibration checking device 100 with controlled humidity is provided. The controlled humidity calibration checking device 100 may be mounted to the housing 24 or an external location but is operatively attached to the probe assembly 40. The controlled humidity calibration checking device 100 serves to periodically remove or dislodge the mercury analyte that was removed from the exhaust gas and accumulated on surfaces of the probe assembly 40. Thus, the controlled humidity calibration checking device 100 provides the probe assembly 40 that is relatively maintenance free and permits a representative sample from the exhaust flue gas flow to be collected to assure the accuracy and precision of the CEMS 20.

The controlled humidity calibration checking device 100 according to one aspect of the invention includes an elemental mercury sample source 102. The elemental mercury sample source 102 is fluidly connected to a humidifier 104 in any suitable form, such as a vaporizer or permeation tube. A source of moisture 106 is fluidly connected to the humidifier 104 through a mass flow controller 108. The humidifier is fluidly connected to the probe assembly 40 at the probe tip 42 by a line 120. An air cleanup panel 140 is fluidly connected to the probe tip 42 by line 142.

The controlled humidity calibration checking device 100 provides a humidified sample of a known quantity of elemental mercury and at a known flow rate to the probe tip 42. The level of humidity is in the range of 2 to 33 percent and preferably maintained in the range of 5-20 percent. It has been found that a humidified sample of elemental mercury provides more accurate and precise measure of mercury than by supplying a dry sample. This is believed due to a cleansing action that the supplied moisture has on the particulates and other undesirable material on the wetted surfaces (where the analyte comes into contact) of the probe assembly 40.

The elemental mercury sample source 102 of the controlled humidity calibration checking device 100 provides a flow of a known concentration of elemental mercury to the humidifier 104 at a known flow rate. The concentration of elemental mercury is, for example 10 micrograms per cubic meter of air ($\mu g/m^3$). This sample of elemental mercury passes through the humidifier 104. In the mercury sample source 102 there are two mass flow controllers (not shown) through which air is passed. One measures air on a very small scale, about 0-40 ml/minute and this air is fed to a heated reservoir of elemental mercury. This small amount of gaseous mercury is mixed with a larger volume of air (0-40 SLPM) that is measured by another gas mass flow controller. In both cases these mass flow controllers are upstream of a mercury reservoir and a mixing chamber because it is undesirable for the elemental mercury gas to come into contact with any metal material inside the mass flow controllers.

A desired amount of moisture in the form of a liquid such as water, initially is provided from the source 106 at a temperature above it's dew point such as about 70° C. It is preferred that the water stay in vapor form and when the humidified sample is delivered to the probe 40 the humidified gas should be similar in temperature that the probe components. Thus, the components of the probe 40 are heated in order to prevent thermal shock to the probe components. The components from the humidifier 104 to the probe 40, such as the line 120 are kept heated at 180° C. or higher.

The mass controller 108 meters the amount of water provided to the humidifier 104. The water is delivered to the elemental mercury flowing through the humidifier 104 as moisture vapor. The moisture is carried along with the mercury sample to the probe assembly 40 via line 120. The moisture acts to cleanse the accumulated mercury that was adsorbed onto the surfaces of the probe assembly 40 and particles adhered to the probe components. The moisture acts to cleanse particulates and other undesirable material that are adhering to the wetted surfaces of the probe to eliminate the adsorption of elemental mercury from the stack gas sample or the calibrated elemental mercury gas. An accurate measure of the concentration of the gaseous species of mercury is provided. The sample of elemental mercury that the gas analyzer measures is representative of the concentration delivered by the mercury sample source 102.

The purpose of this is to provide "cleansing" material along with the elemental mercury calibration gas to wash away any particulates and other undesirable material that cause the adsorption of elemental mercury. The removal of elemental mercury from the sample gas, whether it is stack gas sample or calibration sample, affects the accuracy and precision of the measurement of the elemental mercury. By preventing this removal a more accurate and precise measurement of the analyte is made for the stack gas sample and calibration gas.

To insure that the gas analyzer provides the most precise and accurate measurement of the mercury analyte, a controlled humidity calibration checking system 100 is provided. The controlled humidity calibration checking system 100 is in fluid communication with the probe assembly 40. The controlled humidity calibration checking system 100 includes the mercury sample source 102 that provides a known concentration of calibration material to be measured by the gas analyzer. The humidifier 104 is associated with the mercury sample source 102 to provide moisture to a flow of calibration material. The moisture acts to cleanse particulates and other undesirable material from the probe 40 and thereby provide an accurate measure of the concentration of the mercury calibration material and samples from the flue gas stream.

A supply system 160 (FIG. 1) according to one aspect of the invention is operatively connected with the humidifier 104 to provide a desired amount of a liquid to the humidifier. The supply system 160 also includes a pressurized gas supplied from a source 162, such as a storage tank, compressor or facility air supply. The gas source 162 provides overpressure to the water source 106. The driving force of the overpressure acts to deliver water from the source 106 to the humidifier 104. The overpressure drives water from the source 106 to the humidifier 104 when the mass control device 108 permits flow.

The continuous emissions monitoring system 20 may also include a control system 164 for monitoring the humidity delivered from the humidifier 104 and controlling the amount of moisture delivered to the humidifier. The humidity delivered by the humidifier 104 is calculated based on the liquid flow measured with the liquid mass flow controller 108 and the gas flow measured by a gas mass flow controller in the mercury sample source 102. Knowing the temperature of the humidified gas and the mass flow of the liquid and gas provides an accurate calculation of the humidity delivered by the humidifier 104. This calculation is accurate enough for purposes of "cleaning" the surfaces of the probe 40. This calculation can be communicated to the controller 168, such as a PLC, and control of the flow of water to the humidifier 104 and thus humidity delivered by the humidifier.

The control system 164 includes an optional sensor 166 in line 120 that measures humidity established by the humidifier 104. The sensor 166 communicates the humidity measurement to a controller 168 that compares the measurement to upper and lower desired limits. The controller 168 them signals the mass controller 108 to change state, if needed, in order to maintain the humidity delivered by the humidifier 104 between the desired limits.

Figure 2:
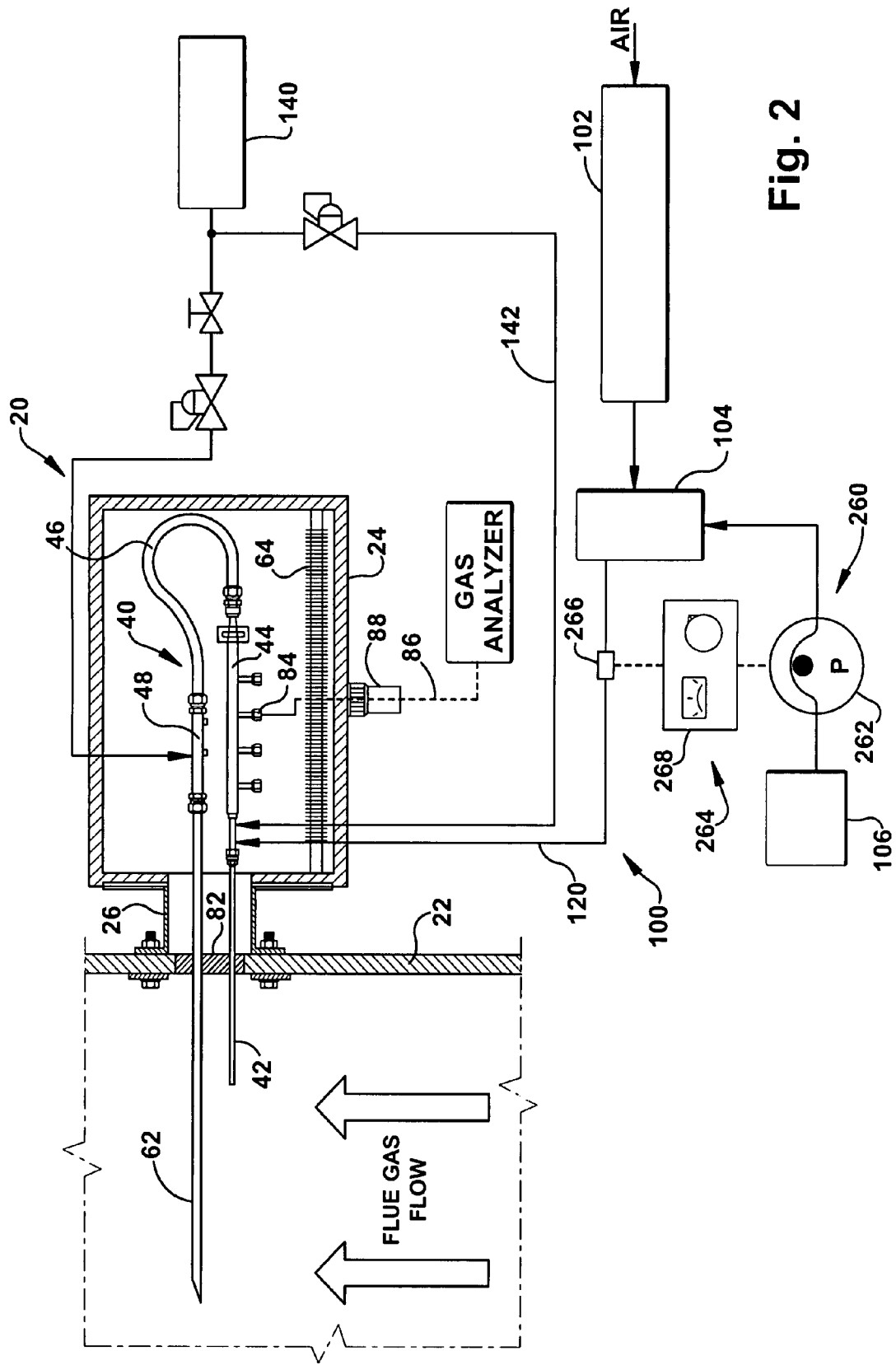
FIG. 2 is a schematic illustration similar to FIG. 1, of a system for controlled humidification of calibration checking equipment in a continuous emissions monitoring system according to another aspect of the invention.

The gas sample acquisition apparatus 20 is illustrated in FIG. 2, and includes structure according to another aspect of the invention for checking the calibration of a continuous emissions monitoring system (CEMS). To minimize particulate matter from accumulating on surfaces of the components of the probe assembly 40 of the gas sample acquisition apparatus 20 has a controlled humidity calibration checking device 100. The controlled humidity calibration checking device 100 may be mounted to the housing 24 or an external location but is operatively attached to the component of the probe assembly 40. The controlled humidity calibration checking device 100 serves to periodically remove or dislodge the mercury that was removed from the exhaust gas and accumulated on surfaces of the probe assembly 40. Thus, the probe assembly 40 is relatively maintenance free and provides a representative sample from the exhaust flue gas flow to assure the accuracy and precision of the CEMS. The probe assembly 40 can be either of an inertial filter design (as depicted in the Figures) or a dilution extractive design. The application of this invention is not restricted to the type of probe design.

The controlled humidity calibration checking device 100 includes an elemental mercury sample source 102. The elemental mercury sample source 102 is fluidly connected to the humidifier 104. The humidifier 104 may be in the form of a vaporizer or permeation tube. A source of moisture 106 is fluidly connected to the humidifier 104. The humidifier 104 is fluidly connected to the probe assembly 40 at the probe tip 42 by a line 120. An air cleanup panel 140 is fluidly connected to the probe tip 42 by line 142.

The controlled humidity calibration checking device 100 provides a humidified sample of a known quantity of elemental mercury to the probe tip 42. The level of humidity is in the range of 2 to 33 percent and preferably in the range of 5-20 percent. It has been found that a humidified sample of elemental mercury provides more accurate and precise measure of mercury than by supplying a dry sample. This is believed due to a cleansing action of the moisture on the particulates and other undesirable material accumulated on the surfaces of the probe assembly 40.

The elemental mercury sample source 102 of the controlled humidity calibration checking device 100 provides a flow of a known concentration of elemental mercury to the humidifier 104. The concentration of elemental mercury is, for example 10 micrograms per cubic meter of air ($\mu g/m^3$). This sample of elemental mercury passes through the permeation tube from of the humidifier 104. A desired amount of moisture is provided from the source 106, such as liquid water. The water is delivered to the flow of elemental mercury sample as moisture vapor. The moisture is carried along with the mercury sample to the probe assembly 40 via line 120. The moisture acts to cleanse the accumulated mercury that was adsorbed onto the surfaces of the probe assembly 40. Thus, the sample of elemental mercury that the gas analyzer measures is representative of the concentration delivered by the source 102.

To insure that the gas analyzer provides the most precise and accurate measurement of the analyte, a controlled humidity calibration checking system 100 is provided. The controlled humidity calibration checking system 100 is in fluid communication with the probe 40. The controlled humidity calibration checking system 100 includes a source that provides a known concentration of mercury calibration material to be measured by the analyzer. The humidifier 104 is associated with the source to provide moisture to a flow of mercury calibration material. The moisture acts to cleanse particulates and other undesirable material from the probe that could cause the adsorption of elemental mercury onto the wetted surfaces of the probe and thereby provide an accurate measure of the concentration of the mercury calibration material and concentration frequency in the sample gas.

A supply system 260 (FIG. 2) according to another aspect of the invention is operatively connected with the humidifier 104 to provide a desired amount of a liquid to the humidifier. The supply system 260 includes a pump 262. The pump 262 may be any suitable pump type. One satisfactory type of pump 262 is a peristaltic pump. The pump 262 provides a driving force to water delivered from the water source 106. The pump 262 acts to deliver metered water from the source 106 to the Humidifier 104.

The continuous emissions monitoring system 20 may further include a control system 264 for monitoring the humidity delivered from the humidifier and controlling the amount of moisture delivered to the humidifier 104. The humidity delivered by the humidifier 104 is calculated based on the liquid flow from the pump 262 and the gas flow measured by a gas mass flow controller in the mercury sample source 102. Knowing the temperature of the humidified gas and the mass flow of the liquid and gas provides an accurate calculation of the humidity delivered by the humidifier 104. This calculation is accurate enough for purposes of "cleaning" the surfaces of the probe 40. This calculation can be communicated to the controller 268, such as a PLC, and control of the flow of water to the humidifier 104 and thus humidity delivered by the humidifier.

The control system 264 may also include an optional sensor 266 in line 120 that measures humidity established by the humidifier 104. The sensor 266 communicates the humidity measurement to a controller 268 that compares the measurement to upper and lower desired limits. The controller 268 then signals the pump 262 to change state, if needed, in order to maintain the humidity delivered by the humidifier 104 between the desired limits.

From the above description of at least one preferred embodiment of the invention, it will be appreciated that improvements, changes and modifications made be made. Such improvements, changes and modifications are intended to be covered by the appended claims.

What is claimed is:

1. A continuous emissions monitoring system that is in fluid communication with a flue stack conducting exhaust gas from a combustion source, the continuous emissions monitoring system comprising:

an analyzer for measuring concentrations of an analyte present in the exhaust gas;

a probe in fluid communication with the flue stack, the probe having an inlet to acquire a sample of exhaust gas from the flue stack, the probe also having an outlet to return the sample to the flue stack, the probe being in fluid communication with the analyzer, and the probe inlet being located upstream of the analyzer, the probe tending to remove analyte from the sample;

a calibration checking system in fluid communication with the probe at a location downstream of the probe inlet and upstream of the analyzer, the calibration checking system including:

a source that provides a gas flow of a known concentration of calibration material to be measured by the analyzer, the calibration material being chemically the same as the analyte;

a supply system including a water source and a pressurized gas located upstream of the water source, the supply system providing a water flow to a mass flow controller; and a humidifier that combines the gas flow and the water flow from the mass flow controller to provide moisture to the calibration material, the moisture acting to remove accumulated analyte from the probe and thereby enable an accurate measurement of the concentration of the calibration material; and an air cleanup panel fluidly connected to the probe at a first location upstream of the analyzer and at a second location downstream of the analyzer.

2. The continuous emissions monitoring system of claim 1 further including a control system for monitoring the humidity delivered from the humidifier and controlling the amount of moisture delivered to the humidifier.

3. The continuous emissions monitoring system of claim 1 wherein the analyte is mercury.

4. A continuous emissions monitoring system that is in fluid communication with a flue stack conducting exhaust gas from a combustion source, the continuous emissions monitoring system comprising:

an analyzer for measuring concentrations of mercury present in the exhaust gas;

a probe in fluid communication with the flue stack to acquire a sample of exhaust gas from the flue stack and in fluid communication with the analyzer, the probe having a probe inlet which is located upstream of the analyzer and an outlet for returning the sample to the flue stack;

a calibration checking system in fluid communication with the probe, the calibration checking system being upstream of the analyzer and downstream of the probe inlet, and including a source that provides a gas flow of a mercury calibration material to be measured by the analyzer;

a humidifier associated with the source that provides moisture to the gas flow of mercury calibration material, the moisture acting to cleanse mercury from the probe and thereby enable an accurate measurement of the concentration of the mercury calibration material;

a supply system operatively connected with the humidifier to provide a desired amount of a liquid to the humidifier, the supply system including a liquid source, a pressurized gas located upstream of the liquid source, and a mass flow controller to move the liquid to the humidifier; and an air cleanup panel fluidly connected to the probe at a first location upstream of the analyzer and at a second location downstream of the analyzer.

5. The continuous emissions monitoring system of claim 4 further including a control system for monitoring the humidity delivered from the humidifier and controlling the amount of moisture delivered to the humidifier.

* * * * *